(12) United States Patent
Yeomans et al.

(10) Patent No.: US 9,320,867 B2
(45) Date of Patent: Apr. 26, 2016

(54) CONNECTION SYSTEM

(71) Applicant: Pall Corporation, Port Washington, NY (US)

(72) Inventors: Heather Yeomans, Hants (GB); Alastair Hunter, Hants (GB)

(73) Assignee: Pall Corporation, Port Washington, NY (US)

( * ) Notice: Subject to any disclaimer, the term of this patent is extended or adjusted under 35 U.S.C. 154(b) by 317 days.

(21) Appl. No.: 13/900,009

(22) Filed: May 22, 2013

(65) Prior Publication Data

US 2014/0345611 A1    Nov. 27, 2014

(51) Int. Cl.
  *A61M 16/18*    (2006.01)
  *A61M 16/08*    (2006.01)
  (Continued)

(52) U.S. Cl.
  CPC .......... *A61M 16/085* (2014.02); *A61M 16/0045* (2013.01); *A61M 16/01* (2013.01);
  (Continued)

(58) Field of Classification Search
  CPC .......... A61M 16/0045; A61M 16/009; A61M 16/01; A61M 16/08; A61M 16/0816; A61M 16/0841; A61M 16/085; A61M 16/0858; A61M 16/0875; A61M 16/0883; A61M 16/0891; A61M 16/18; A61M 16/186; A61M 2016/1035; A61M 39/08; A61M 39/10; A61M 39/105; A61M 39/12; A61M 2039/082; A61M 2039/1027; A61M 2039/1055; A61M 2039/1077; A61M 2202/0241; A61M 2205/3331; A61M 2205/3344; F16L 39/00; F16L 39/005

USPC ............. 128/202.27, 203.24, 207.14, 207.15; 285/124.1–124.5
See application file for complete search history.

(56) References Cited

U.S. PATENT DOCUMENTS 3,469,863 A * 9/1969 Riester .................... F16L 37/56
                                                    277/322
4,059,657 A    11/1977 Hay
(Continued)

FOREIGN PATENT DOCUMENTS

JP    06-315474 A2    11/1994
JP    2008-188360 A    8/2008
(Continued)

OTHER PUBLICATIONS

European Search Report, Application No. 14165120.8 dated Sep. 17, 2014.
(Continued)

*Primary Examiner* — Tan-Uyen (Jackie) T Ho
*Assistant Examiner* — Joseph D Boecker
(74) *Attorney, Agent, or Firm* — Jeremy Jay

(57) ABSTRACT

A breathing filter system for a vaporizer system includes a connector comprising a first portion comprising a conduit manifold comprising having lumens; a second portion comprising an interface plug comprising a plug end; an external surface comprising ribs and grooves, the second portion further comprising openings in communication with the lumens of the conduits, each lumen communicating with a single opening, the openings being arranged in the grooves; and, a breathing filter system assembly comprising a housing comprising a first section including a first port, a second section including a second port, providing a bi-directional flow path between the ports; a gas reflection device, and a heat and moisture exchanging breathing filter, disposed in the housing across the fluid flow path, the breathing filter arranged in the first section, and the gas reflection device arranged in the second section; wherein the housing is in communication with the first portion.

11 Claims, 10 Drawing Sheets

Figure 1:
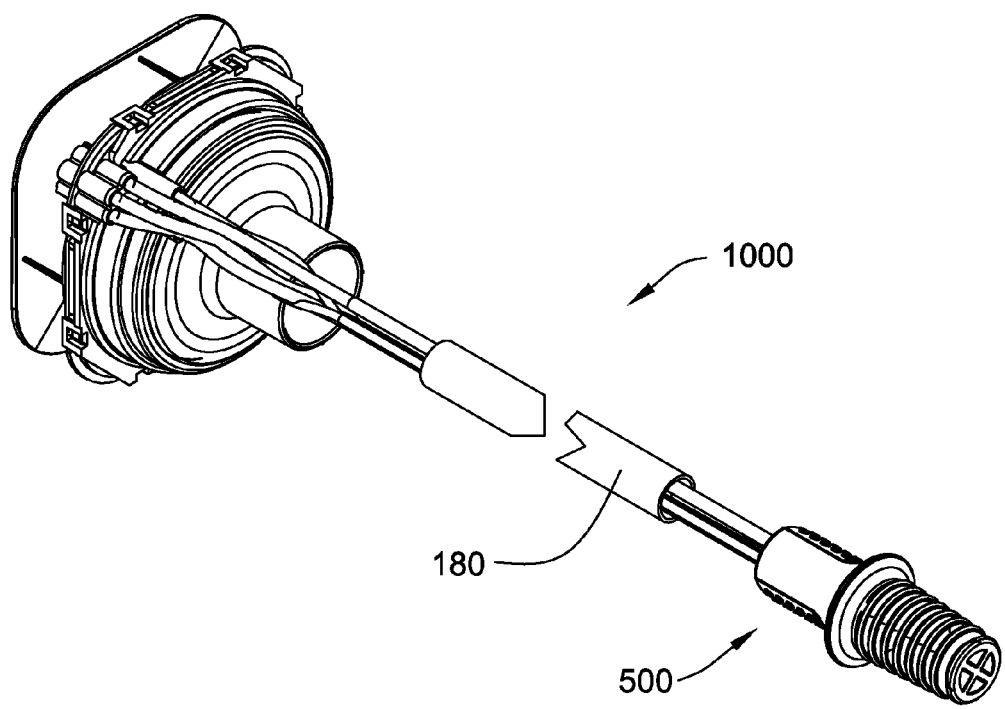

(51) Int. Cl.
*A61M 16/01* (2006.01)
*A61M 16/10* (2006.01)
*A61M 16/00* (2006.01)

(52) U.S. Cl.
CPC ....... *A61M16/0816* (2013.01); *A61M 16/0858* (2014.02); *A61M 16/1045* (2013.01); *A61M 16/18* (2013.01); *A61M 2016/003* (2013.01); *A61M 2016/0027* (2013.01); *A61M 2016/1035* (2013.01); *A61M 2202/0241* (2013.01); *A61M 2205/273* (2013.01); *A61M 2205/3331* (2013.01); *A61M 2205/50* (2013.01); *A61M 2205/6045* (2013.01); *A61M 2205/6054* (2013.01)

(56) References Cited

U.S. PATENT DOCUMENTS

| | | | |
|---|---|---|---|
| 4,850,371 A | 7/1989 | Broadhurst et al. | |
| 4,921,010 A * | 5/1990 | Spirer | F16L 39/04 137/580 |
| 5,111,827 A | 5/1992 | Rantala | |
| 5,810,001 A * | 9/1998 | Genga | A61M 16/183 128/202.27 |
| 5,823,811 A * | 10/1998 | Blanchfield | H01R 13/5025 439/274 |
| 5,920,934 A * | 7/1999 | Hannagan | A61G 7/05776 137/625.21 |
| 6,089,105 A | 7/2000 | Ricciardelli | |
| 6,095,135 A * | 8/2000 | Clawson | A61M 16/08 128/201.13 |
| 6,131,571 A | 10/2000 | Lampotang et al. | |
| 6,206,002 B1 * | 3/2001 | Lambert | A61M 16/009 128/203.13 |
| 6,668,828 B1 | 12/2003 | Figley et al. | |
| 6,850,882 B1 * | 2/2005 | Rothenberg | G10L 25/00 704/211 |
| 7,731,739 B2 * | 6/2010 | Schock | A61F 7/00 607/104 |
| 8,424,920 B2 * | 4/2013 | Gilbreath | F16L 37/088 285/124.3 |
| 2003/0122374 A1 | 7/2003 | Ouchi et al. | |
| 2004/0149281 A1 * | 8/2004 | Ahlmen | A61M 16/104 128/203.12 |
| 2004/0222560 A1 * | 11/2004 | Louviere | B29C 45/26 264/297.2 |
| 2005/0166917 A1 * | 8/2005 | Ahlmen | A61M 16/009 128/203.12 |
| 2006/0042631 A1 * | 3/2006 | Martin | A61B 5/0836 128/207.18 |
| 2006/0264909 A1 * | 11/2006 | Fangrow | A61M 39/26 604/539 |
| 2007/0062535 A1 * | 3/2007 | Psaros | A61M 16/0057 128/205.28 |
| 2007/0135757 A1 | 6/2007 | Acker et al. | |
| 2008/0319433 A1 | 12/2008 | Geiselhart | |
| 2009/0051164 A1 | 2/2009 | Lirsch et al. | |
| 2009/0095296 A1 * | 4/2009 | Wruck | A61M 16/009 128/203.27 |
| 2009/0137951 A1 * | 5/2009 | Buisson | A61M 5/1408 604/87 |
| 2009/0181572 A1 * | 7/2009 | Tracy | G06K 16/07732 439/447 |
| 2009/0250054 A1 * | 10/2009 | Loncar | A61M 16/01 128/203.14 |
| 2012/0016345 A1 * | 1/2012 | Carter | A61M 39/10 604/533 |
| 2012/0031402 A1 * | 2/2012 | Loncar | A61M 16/18 128/203.14 |
| 2013/0147185 A1 * | 6/2013 | Tsao | A61M 39/1011 285/120.1 |
| 2015/0059755 A1 * | 3/2015 | Bassin | A61B 5/4818 128/204.23 |

FOREIGN PATENT DOCUMENTS

| | | |
|---|---|---|
| WO | WO 95/18644 A1 | 7/1995 |
| WO | WO 2005/110200 A1 | 11/2005 |
| WO | WO 2009/033462 A1 | 3/2009 |
| WO | WO 2009/081196 A1 | 7/2009 |
| WO | WO 2009/115076 A1 | 9/2009 |

OTHER PUBLICATIONS

Singapore Search Report, Application No. 10201401655R, mailed Sep. 26, 2014.
Office Action, Counterpart Japanese Application P2014-086637 mailed Mar. 24, 2015.

* cited by examiner

CONNECTION SYSTEM

BACKGROUND OF THE INVENTION

Electronic vaporizer systems can allow the user to set a desired concentration of volatile anesthetic gas to be delivered from a gas controller and through a breathing filter system to a patient. However, there is a need for improved connectors between the gas controller and the breathing filter system communicating with the patient.

BRIEF SUMMARY OF THE INVENTION

An embodiment of the invention provides a connector for use in an electronic vaporizer system comprising (a) a first portion comprising an conduit manifold, the conduit manifold comprising a plurality of separate conduits, each conduit having an internal lumen; and, (b) a second portion comprising (i) an interface plug comprising an interface plug end; and, (ii) an external surface comprising a plurality of ribs and grooves, the second portion further comprising isolated openings in fluid communication with the internal lumens of the separate conduits, each lumen communicating with a single isolated opening, the openings being arranged in the grooves.

BRIEF DESCRIPTION OF THE SEVERAL VIEWS OF THE DRAWING(S)

FIG. 1 shows a perspective view of an embodiment of the connector of the present invention, the connector comprising a first portion and a second portion, as well as a rigid section and an outer shell.

Figure 2A:
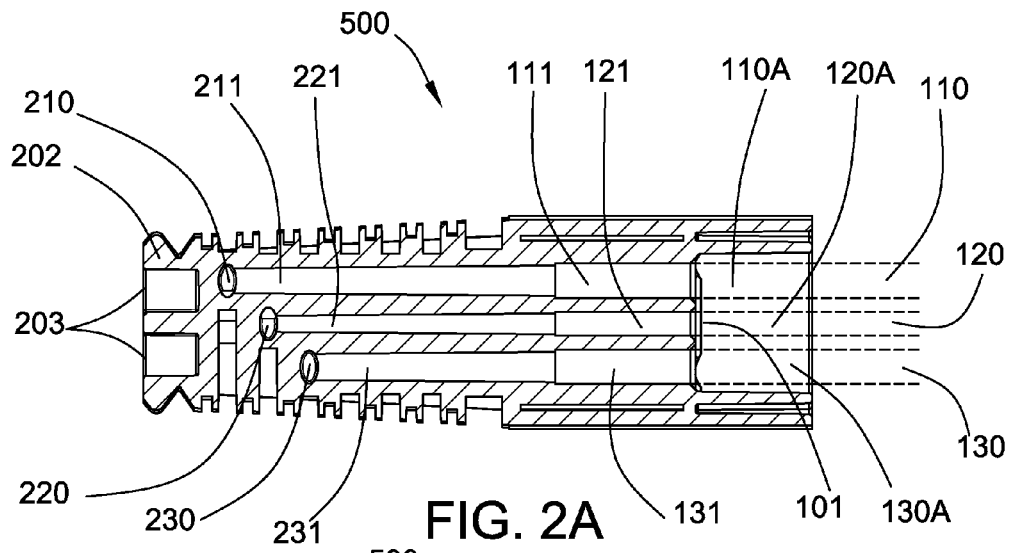
Figure 2B:
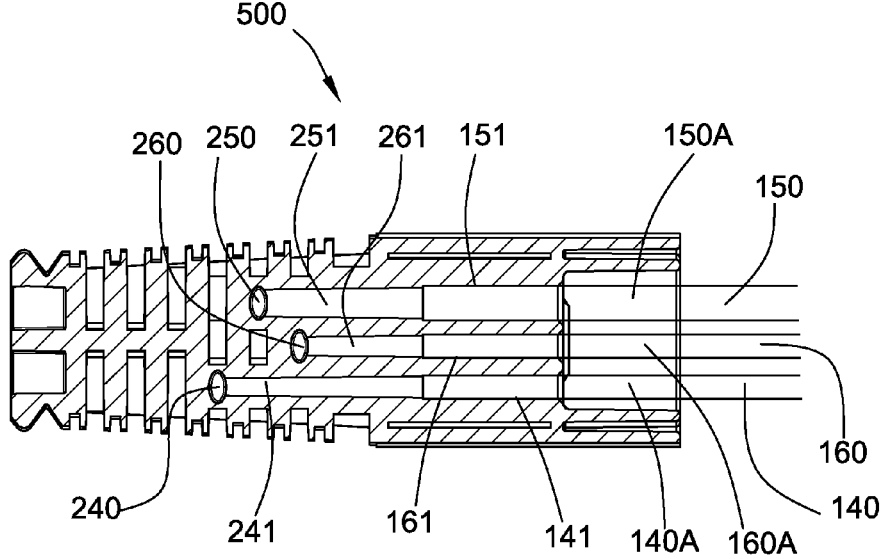
Figure 2C:
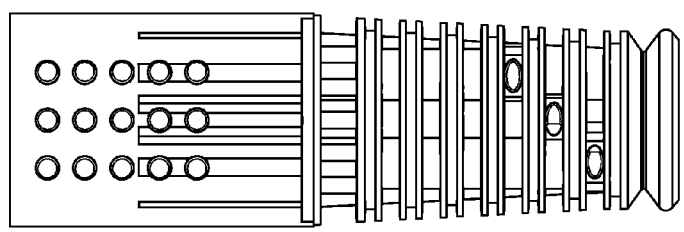
Figure 2D:
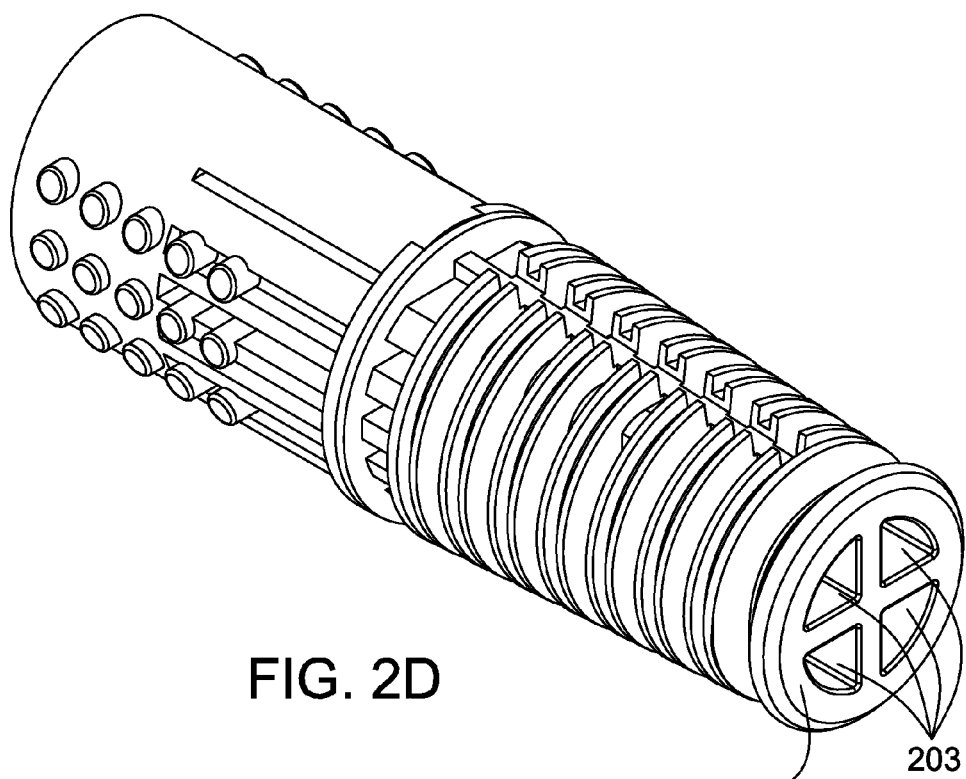
Figure 2E:
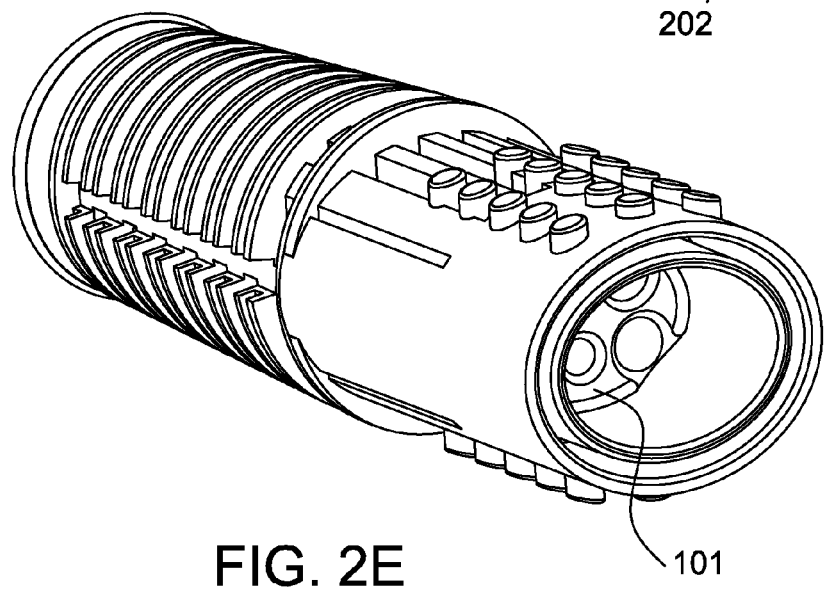

FIG. 2 shows several views of the rigid section shown in FIG. 1, including two longitudinal cross-sectional views (FIGS. 2A and 2B, wherein the rigid section has been rotated to show different isolated openings in the second portion, and section of the fluid flow paths communicating with the openings; the Figures also showing several conduits), a top view (FIG. 2C), and perspective views from the interface plug end (FIG. 2D) and the conduit manifold end (FIG. 2E).

FIG. 3 shows the rigid sections shown in FIG. 2 as well as the outer shell. FIG. 3A shows a longitudinal cross-sectional view, FIG. 3B shows a top view, and FIG. 3C shows a lateral cross-sectional view, also showing 6 ports, wherein 3 ports have larger internal diameters than the other 3 ports. FIGS. 3D and 3E perspective views from the interface plug end, and the conduit manifold end, respectively.

Figure 4:
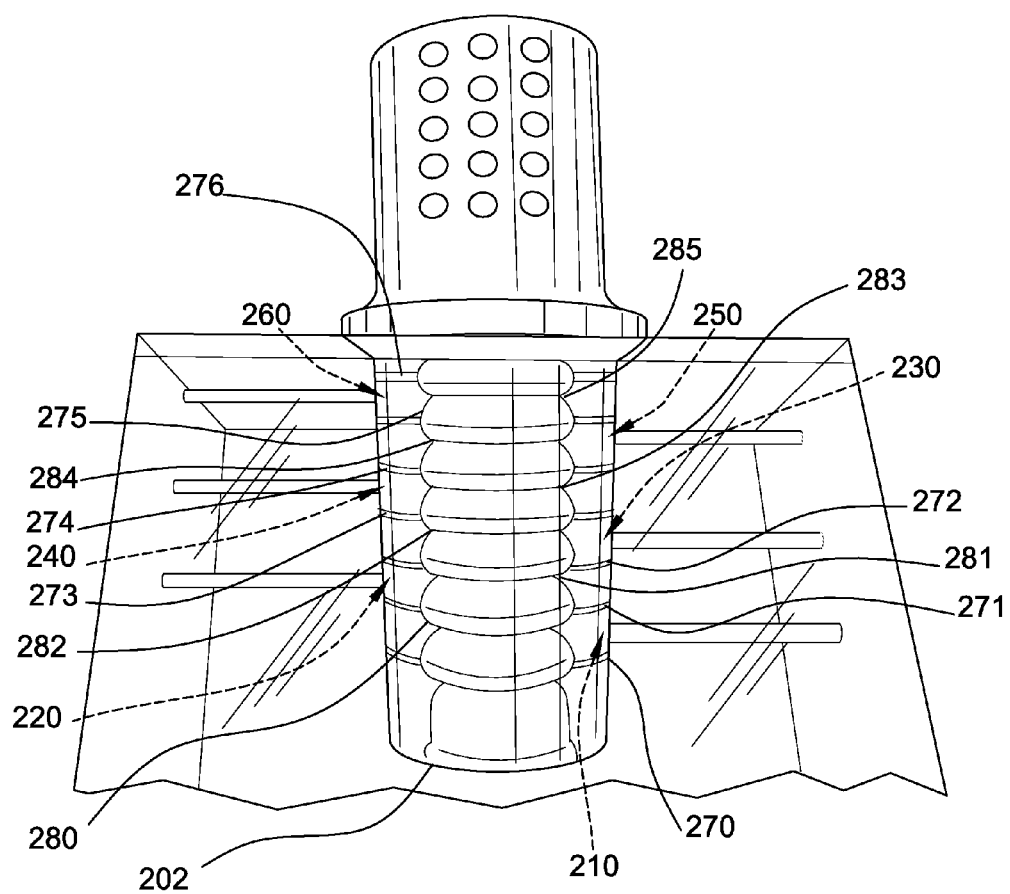

FIG. 4 diagrammatically illustrates an interface plug end of the second portion connected to a receiving portion of a gas controller, also showing fluid communication between the 6 openings in the second portion and the respective 6 ports of the controller, wherein each opening is separate and independent of the other openings, and each port is separate and independent from the other ports, and the respective pair of an opening and a port do not communicate with any other opening or port.

Figure 5A:
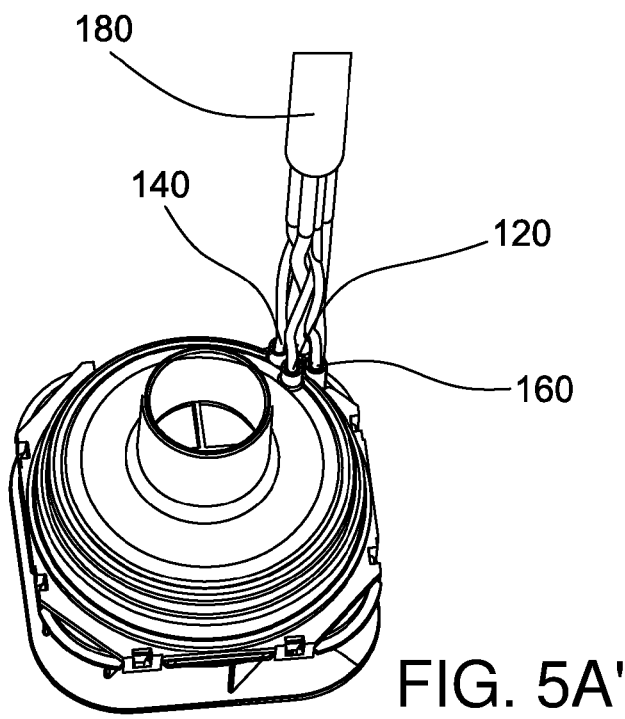
Figure 5A:
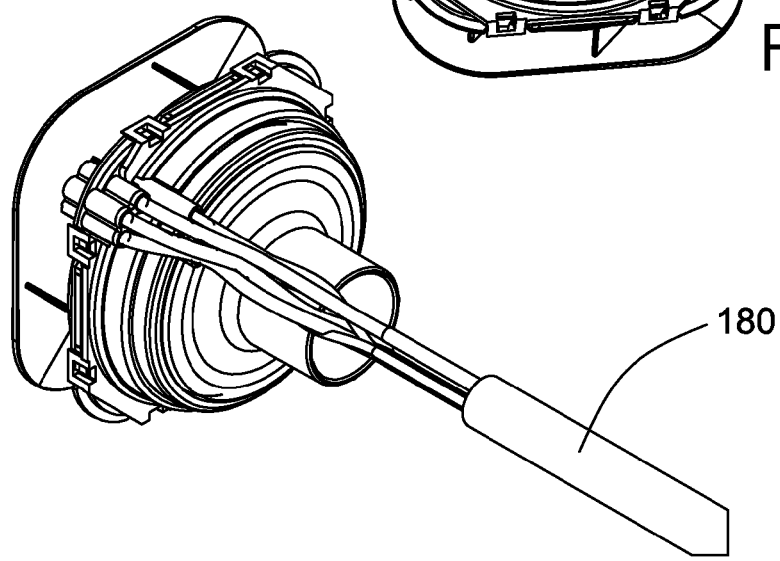
Figure 5B:
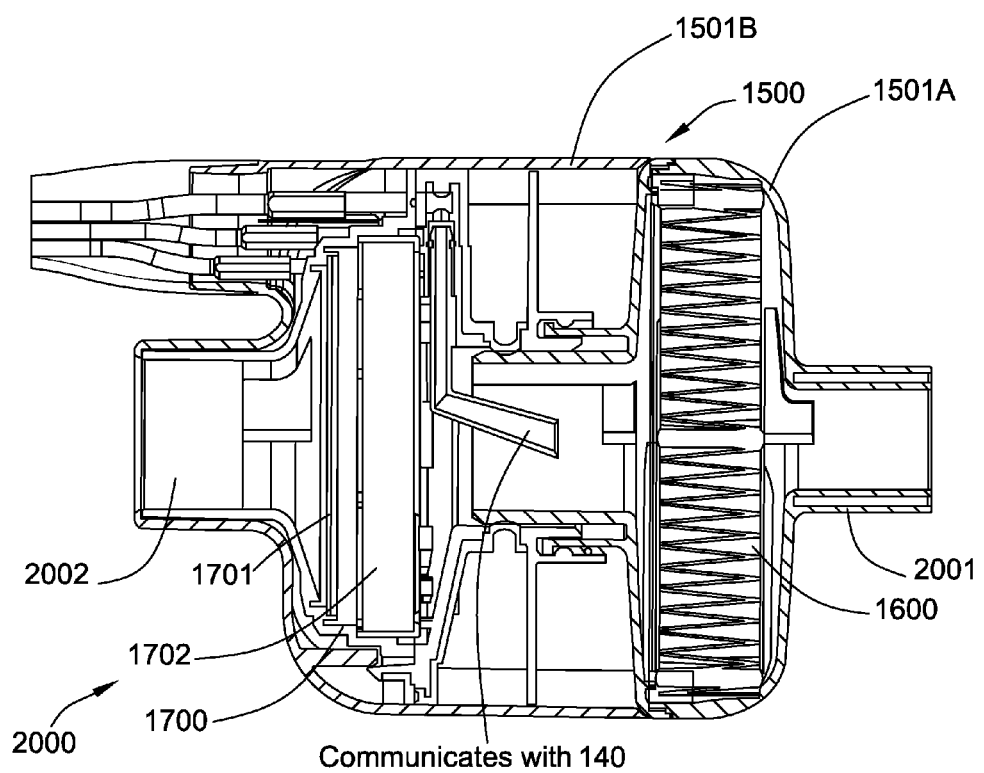

FIGS. 5A, 5A' and 5B show various views illustrating the connection of the 6 conduits to a breathing filter system assembly comprising a housing, a breathing filter, and a gas reflector. FIG. 5A shows connections to a portion of the breathing filter system assembly housing in perspective view and FIG. 5A' shows connections to a portion of the breathing filter system assembly housing in top view; FIG. 5B shows a cross-sectional view of the breathing filter assembly including the housing, a breathing filter, and the gas reflector, wherein the gas reflector comprises a flow detection mesh and a carbon pack.

Figure 6:
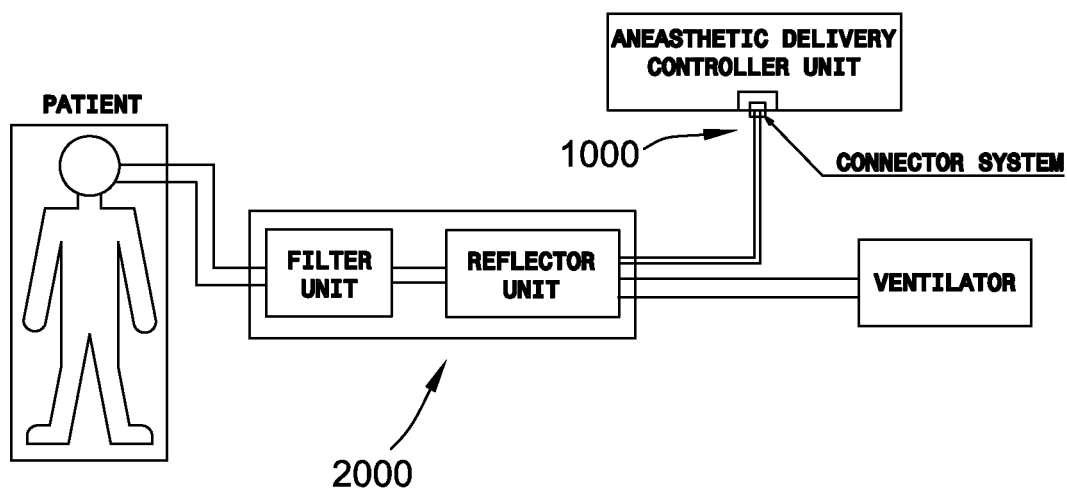

FIG. 6 diagrammatically illustrates an electronic vaporizer system, including a connector according to the invention, in communication with an electronic gas controller, and a breathing filter assembly, wherein the breathing filter assembly is in communication with a ventilator and a patient.

DETAILED DESCRIPTION OF THE INVENTION

Advantageously, connectors according to the invention can be used without a specific user- or device-based orientation, and the connection can be freely rotatable. It is especially useful in a system including a gas controller, wherein the system measures a patient's breathing activities and lung volumes, and, based on the measured volumes, patient characteristics (e.g., weight) and on the desired concentration of volatile anesthetic gas, calculates the necessary amount of volatile anesthetic gas to be added to the breathing gas of the patient, resulting in delivery of the desired concentration of volatile anesthetic gas to a patient to provide anaesthesis, analgesia and/or sedation.

Connectors can include any suitable number of conduits, with any combination of internal and external diameters, without cross contamination from the internal lumen of one conduit to the internal lumen of another conduit.

In an embodiment according to the invention, a connector for use in an electronic vaporizer system is provided comprising (a) a first portion comprising an conduit manifold, the conduit manifold comprising a plurality of separate conduits, each conduit having an internal lumen; and (b) a second portion comprising (i) an interface plug comprising an interface plug end; and, (ii) an external surface comprising a plurality of ribs and grooves, the second portion further comprising isolated openings in fluid communication with the internal lumens of the separate conduits, each lumen communicating with a single isolated opening, the openings being arranged in the grooves. Typically, the conduit manifold comprises at least 4 conduits, preferably at least 6 conduits. For example, in an embodiment of the connector, the conduit manifold comprises a conduit for passage of volatile anesthetic (VA) to the patient, a conduit for sampling VA (and preferably, $CO_2$ sampling; typically, also for returning some VA back to the reflector), a conduit for purging VA (typically, also for returning some VA back to the reflector), and at least one conduit for pressure sensing (e.g., measuring pressure drop). Preferably, the connector manifold comprises at least three conduits for pressure sensing (e.g., for respiratory monitoring), for example, a pair of conduits for measuring pressure drop across the flow detection mesh of the gas reflector (e.g., for respiratory monitoring) and a pair of conduits for measuring pressure drop across another component of the gas reflector (e.g., the carbon pack), wherein one of the conduits is used both in measuring pressure drop across the flow detection mesh and measuring pressure drop across another component of the gas reflector (e.g., the conduit is arranged upstream of the other component(s) of the gas reflector and downstream of the flow detection mesh). More preferably, the conduits for passage of VA, sampling VA, and for purging VA, have larger internal diameters than the conduit(s) for pressure sensing.

In some embodiments of the connector, the external surface of the second portion comprises an outside diameter, wherein the outside diameter increases in a direction from the interface plug end toward the first portion, e.g., the second portion includes a taper.

Embodiments of the connector can further comprise an outer cover or sleeve for the plurality of conduits, the outer cover having one end bound to the first portion. In an embodiment, the first portion includes a slot, and the end of the outer cover bound to the first portion is contained in the slot.

Each of the components of the invention will now be described in more detail below, wherein like components have like reference numbers.

In the illustrated embodiments, the connector 1000 comprises (e.g., as shown in FIGS. 2-4) a rigid section or skeleton 500 partially covered with a flexible (preferably soft) shell or overmold 600, wherein the materials used for making the rigid section and shell section are chemically compatible with each other. For example, the rigid section can comprise an insert-molded styrene-based plastic and the outer shell can comprise an elastomeric overmold, wherein the rigid section and shell form a direct physical bond when processed together to form the connector. The rigid section and shell can be prepared by processes known in the art, e.g., insert molding followed by overmolding, or by 2-shot molding, or by co-injection molding.

In the embodiments illustrated in FIGS. 2-4, the rigid section 500 and the outer shell 600 (having an external surface 601) extend from part of the first portion 100 through at least most of the length of the second portion 200 (in the illustrated embodiments, the rigid section extends from at least the conduit manifold 101 of the first portion through the entire length of the second portion). The external surface 601 comprises the first portion outer surface 601A and the second portion outer surface 601B. The external surfaces 601A and 601B can be continuous.

As shown in more detail in FIGS. 2-4, the illustrated first portion 100 comprises an external surface 601A, a conduit manifold 101, and separate conduits 110, 120, 130, 140, 150, 160 communicating with, preferably bonded to, the conduit manifold (in FIG. 2A, conduits 110, 120, and 130 are shown in dotted lines for ease in showing other structures in the first portion). The conduits 110, 120, 130, 140, 150, 160 respectively have internal lumens 110A, 120A, 130A, 140A, 150A, 160A, and internal diameters 110B, 120B, 130B, 140B, 150B, 160B. The illustrated first portion further comprises fluid flow channels 111, 121, 131, 141, 151, 161 in fluid communication with respective conduits. There is no "crosstalk" between the conduits and between the fluid flow channels, e.g., conduit 110 is only in fluid communication with fluid flow channel 111, and neither conduit 110, nor fluid flow channel 111, communicates with another conduit or fluid flow channel. In some embodiments, the conduits and fluid flow channels do not all have the same internal diameters. For example, as shown in FIGS. 2A, 2B, and 3C, internal diameters 110B, 120B, and 130B are larger than internal diameters 140B, 150B, and 160B. A variety of combinations of internal diameters are encompassed in accordance with embodiments of the invention.

Figure 3B:
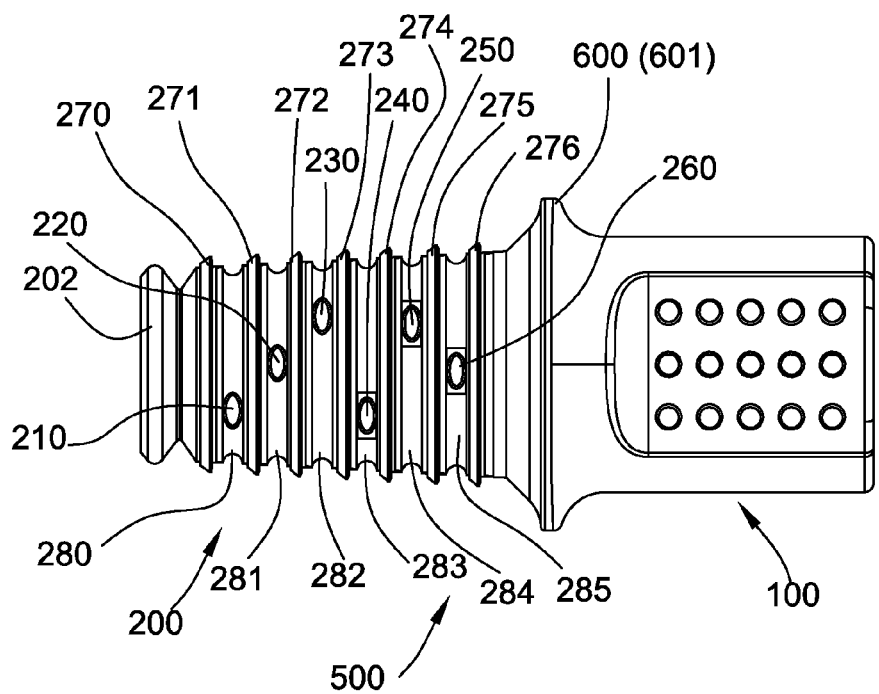
Figure 3A:
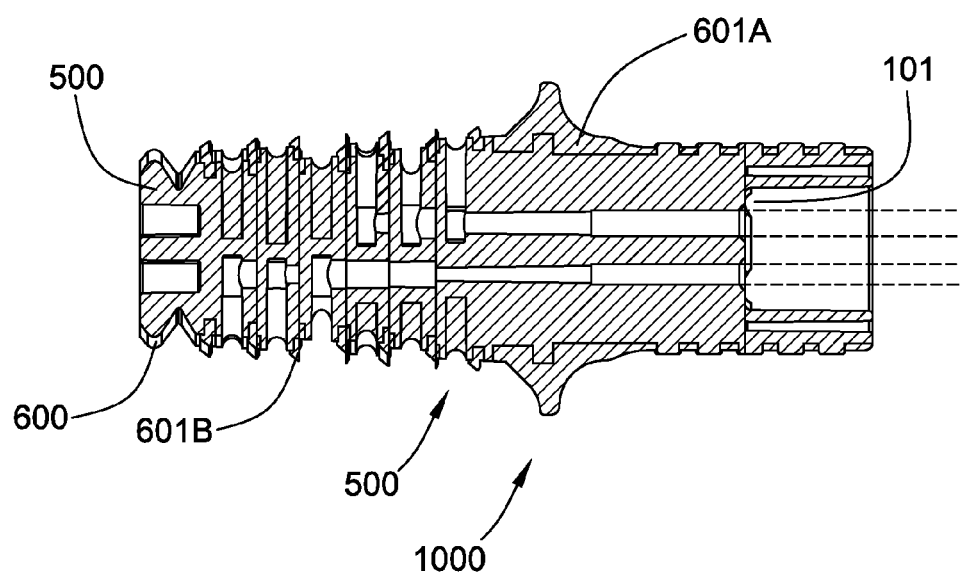
Figure 3C:
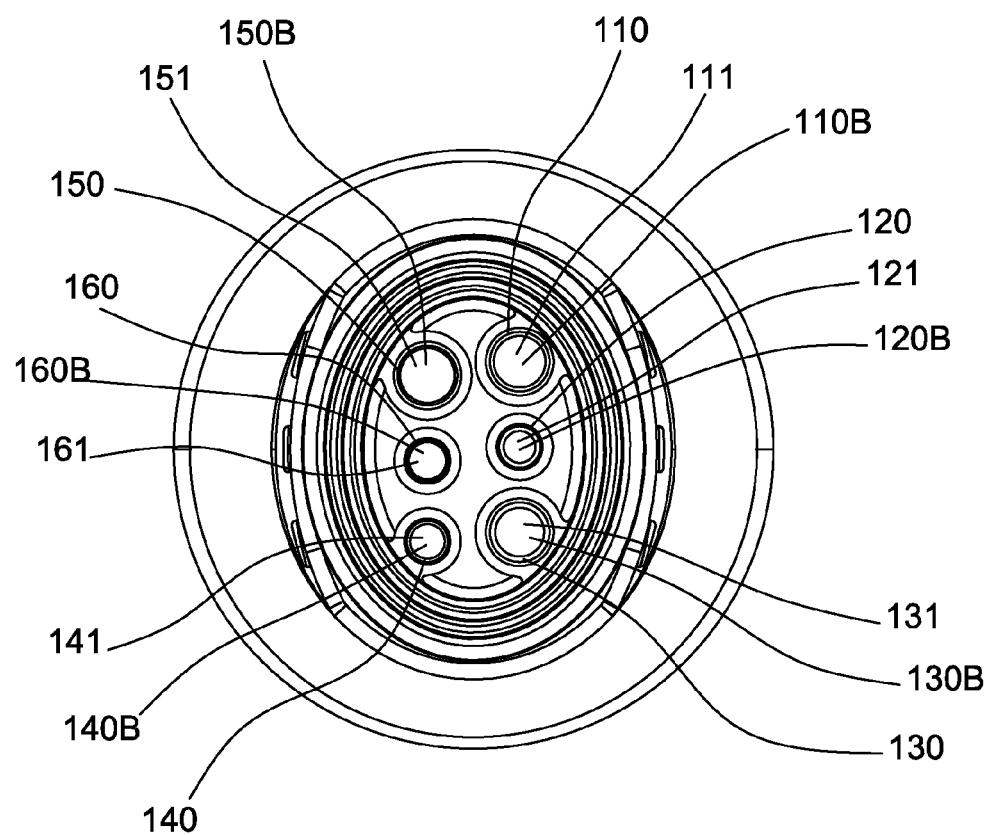
Figure 3D:
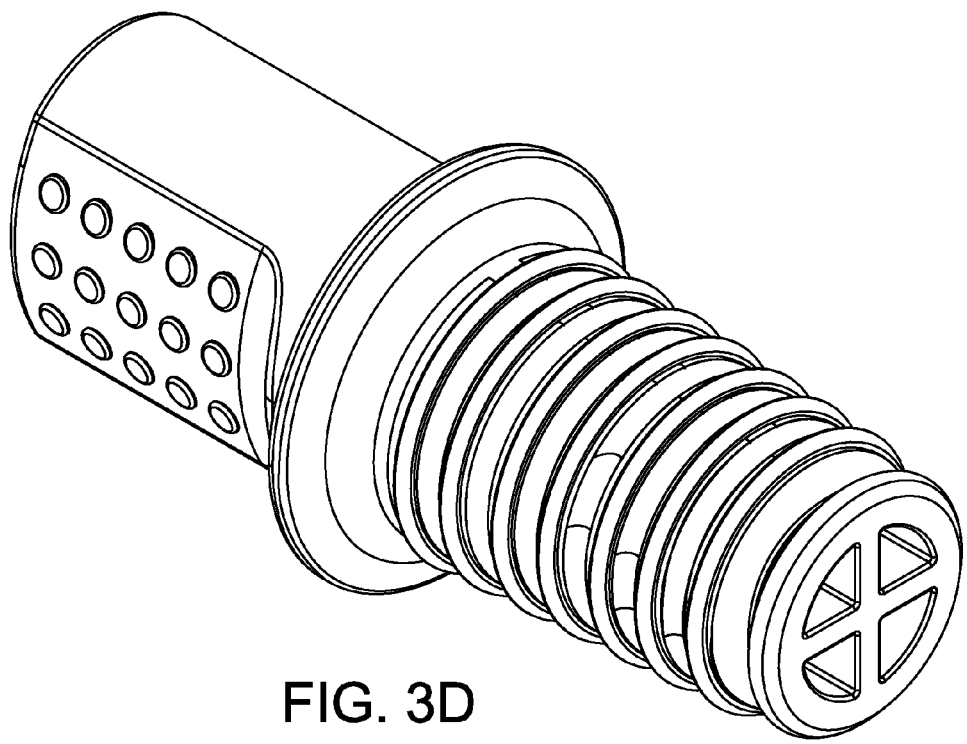
Figure 3E:
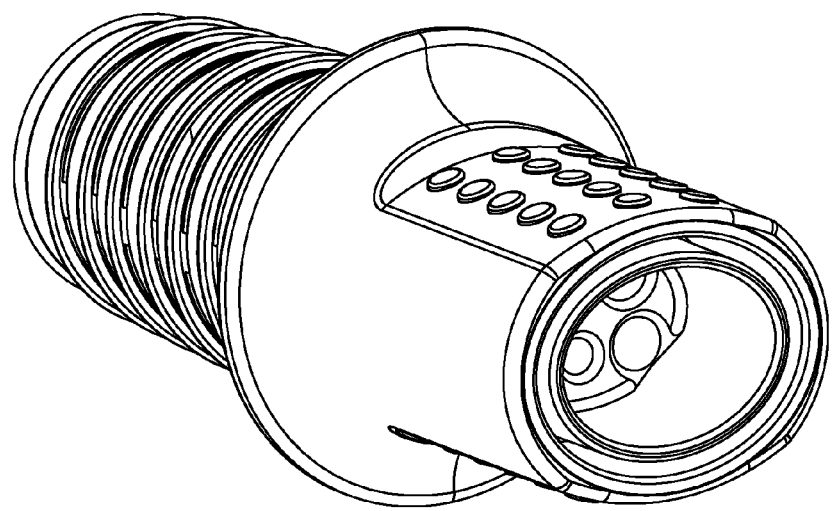

As shown in more detail in FIGS. 3A and 3B, the illustrated second portion 200 comprises an external surface 601B, an interface plug 201 having an interface plug end 202, ribs 270, 271, 272, 273, 274, 275, and 276, grooves 280, 281, 282, 283, 284, and 285 (located in separate grooves), isolated openings 210, 220, 230, 240, 250, and 260, and fluid flow channels 211, 221, 231, 241, 251, and 261.

There is no "crosstalk" between the conduits and between the fluid flow channels, e.g., opening 210 is only in fluid communication with fluid flow channel 211, and neither opening 210, nor fluid flow channel 211, communicates with another opening or fluid flow channel. In the illustrated embodiments, first portion fluid flow channels 111, 121, 131, 141, 151, 161 are in fluid communication with second portion fluid flow channels 211, 221, 231, 241, 251, 261 and thus, there is fluid communication between conduits 110, 120, 130, 140, 150, 160 and isolated openings 210, 220, 230, 240, 250, 260 (via internal lumens 110A, 120A, 130A, 140A, 150A, 160A, fluid flow channels 111, 121, 131, 141, 151, 161, and fluid flow channels 211, 221, 231, 241, 251, 261. In the illustrated embodiments, second portion fluid flow channels 211, 221, 231, 241, 251, 261 extend (via rigid section 500) into the first portion 100, but in other embodiments, the fluid flow channels do not extend that far, or the first portion fluid flow channels can extend into the second portion, or a single set of fluid flow channels extends through the first and second portions. Alternatively, either or both sets of fluid flow channels can be replaced by conduits, e.g., conduits 110, 120, 130, 140, 150, and 160 can extend into the first portion, and if desired, to the openings 210, 220, 230, 240, 250, and 260.

In a preferred embodiment, as shown in FIGS. 3A and 3B, the second portion 200 has an outside diameter, wherein the outside diameter increases in a direction from the interface plug end toward the first portion, e.g., the second portion has a taper.

Advantageously, as shown in FIG. 4, diagrammatically illustrating interface plug end 202 of the second portion connected to the respective receiving portion opening (or receptacle) of a gas controller, the ribs, formed by the second portion, 270, 271, 272, 273, 274, 275, and 276, form circumferential seals with the receiving portion, such that grooves 280, 281, 282, 283, 284, and 285 provide isolated and individual annular compartments. As a result, there is fluid communication between the 6 isolated openings 210, 220, 230, 240, 250, and 260, and the respective 6 isolated openings in the gas controller receiving portion. There is no "crosstalk" between openings, e.g., opening 210 is only in fluid communication with the respective receiving portion opening, and neither opening 210, nor the respective receiving portion opening, communicates with another opening. Moreover, since the circumferential seals provide isolated and individual annular compartments, each pair of openings is encompassed by the same annular compartment, and the plug does not have to have a particular orientation in the receiving portion, e.g., the invention can be used without a specific user- or device-based orientation, and the connection can be freely rotatable.

Optionally, and as shown in FIGS. 2 and 3, the interface plug end 202 further comprises at least one locating element 203, e.g., comprising a hollowed out portion or slot in the rigid portion (preferably, wherein the end of the rigid portion is not covered with an elastomeric material), for engagement by, for example, a member such as a sprung pin in the receiving portion, to ensure full engagement between the interface plug end and the receiving portion. Preferably, the receiving portion includes at least two members engagable with the end of the interface plug and thus the end of the plug comprises at least two locating elements. While the interface plug end can include a hollowed out portion or slot, the end is closed such that there is no communication with the openings 210, 220, 230, 240, 250, and 260. In an additional configuration (not shown), the connector can additionally include, for example, a radio labeling tag such as an RFID device, which can pass information of interest (e.g., manufacturing and/or unit identification information), to the gas controller via interrogating electronics within the gas controller conduit manifold. Advantageously, this information can be used to prevent re-use of a used gas reflector device to which the plug is attached.

In the embodiments illustrated in FIGS. 5A, 5A' and 5B, the other end of the connector 1000 is connected to a breathing filter system assembly 2000 which includes a first main port 2001 and a second main port 2002 defining a bi-directional fluid flow path through the assembly, and a heat and moisture exchanging (HME) microbial barrier filter 1600 and a gas reflector device 1700 (preferably, the gas reflector 1700 reflects exhaled volatile anesthetic back into the next patient inspiration cycle), wherein FIGS. 5A, 5A' and 5B show connections of the connector 1000 to a breathing filter system assembly housing 1500. FIG. 6 shows an illustrative system utilizing the connector.

The illustrated breathing filter system assembly 2000 (shown in more detail in FIG. 5B) comprises a breathing filter system assembly housing 1500 comprising a gas reflector device 1700 (comprising a flow detection mesh 1701 and a carbon pack 1702), that is preferably disposed after use with several patients, and a heat and moisture exchanging (HME) breathing filter 1600 (preferably, a high efficiency hydrophobic porous filter, more preferably, a pleated high efficiency hydrophobic porous filter), that is disposed after use on a single patient. Preferably, the breathing filter system assembly housing 1500 comprises a first section 1501A and a second section 1501B, wherein the breathing filter is disposed in the first section and the gas reflector is disposed in the second section, and the first and second sections are connectable to form a sterilizable single functional unit, while maintaining ISO port compliance. More preferably, the breathing filter system assembly acts as a high efficiency heat and moisture exchanger, such that no additional humidification device is needed. The breathing filter system assembly is positioned between the patient's endotracheal tube or catheter mount and the breathing system's y-piece.

Suitable breathing filters and/or breathing filter media include those available from Pall Corporation (Port Washington, N.Y.) such as a PRO-TEC PF 30S filter, a BB100 Breathing System Filter, a BB50T Breathing Circuit Filter, a HME20Filter, and a HME40 Filter.

Each of conduits 110, 120, 130, 140, 150, and 160, communicates with, and is preferably bonded to, a separate port in the breathing filter assembly housing. Preferably, as shown in FIGS. 1 5A and 5A', the connector 1000 further comprises a cover or sleeve 180 surrounding the conduits. In some embodiments, one end of the cover 180 is bound to the first portion 100, and the other end of the cover is bound to the breathing filter assembly housing. If desired, the first portion can, for example, include a slot, and the end of the outer cover bound to the first portion is contained in the slot. Alternatively, or additionally, in some embodiments, the connector further comprises one or more "anti-kink" protectors, e.g., a soft material covering at least a portion of the cover 180 and a portion of the first portion 100 of the connector, and/or a soft material covering at least a portion of the cover 180 and a portion of the breathing filter assembly system housing.

The conduits and cover, which can be made from a variety of materials (at least the conduits should be made from a material compatible with the fluid(s) and gas(es) present in the breathing filter system), including commercially available materials, can be bound to the connector and breathing filter assembly housing by a variety of processes known in the art, including, for example, adhesive, solvent bonding, and overmolding. The breathing filter system assembly housing can be fabricated from any suitable impervious material, including any impervious thermoplastic material, which is compatible with the fluid(s) and gas(es) present in the breathing system. For example, the housing can be fabricated from a metal, such as stainless steel, or from a polymer. In a preferred embodiment, the housing is a polymer, for example, an acrylic, polypropylene, polystyrene, or a polycarbonated resin.

As noted above, the interface plug connects to a gas controller. The gas controller can be used to measure the patient's breathing activities and volumes and, based on the measured volumes and on the desired concentration of VA, calculate the necessary amount of VA to be added to the breathing gas of the patient, resulting in the delivery of the desired concentration of VA to the patient. Preferably, the controller allows application of the VA only during the diffusion relevant phase of the inspiratory time (e.g., during the phase of highest patient uptake), such that no VA is applied during the expiration time. If desired, VA is delivered without carrier gas into the gas reflector, which acts as a microrebreather, and the gas reflector reflects exhaled VA back into the next inspiration cycle, allowing for a fast patient wash-in, while reducing VA wastage. Suitable gas controllers and their operation are described in, for example, International Publication Nos. 2009/033462 and 2009/115076.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A breathing filter system for use in an electronic vaporizer system comprising:
   (A) a connector comprising:
      (a) a first portion comprising a conduit manifold, the conduit manifold comprising a plurality of separate conduits, each conduit having an internal lumen; and, (b) a second portion comprising
  (i) an interface plug comprising an interface plug end for connection to a receiving portion in an electronic gas controller, the receiving portion including at least two receiving portion members; wherein the interface plug end comprises an end face and at least two locating elements located in the end face, the at least two locating elements each comprising a hollowed out portion for engagement with a respective receiving portion member; and,
  (ii) an external surface comprising a plurality of ribs and grooves, the second portion further comprising isolated openings in fluid communication with the internal lumens of the separate conduits, each lumen fluidly communicating with a single isolated opening without fluid communication with the interface plug end, wherein the interface plug end is closed to such fluid communication, the openings being arranged in the grooves; and,
(B) a breathing filter system assembly comprising:
  (a) a breathing filter assembly housing comprising a first section including a first main port, and a second section including a second main port, providing a bi-directional fluid flow path between the first main port and the second main port; and,
  (b) a gas reflection device comprising a flow detection mesh and a carbon pack; and a heat and moisture exchanging breathing filter, disposed in the breathing filter assembly housing across the bi-directional fluid flow path, wherein the heat and moisture exchanging breathing filter is arranged in the first section, and the gas reflection device is arranged in the second section;
  wherein the breathing filter assembly housing is in fluid communication with the first portion of the connector.

2. The system of claim 1, wherein the plurality of separate conduits comprise at least 4 conduits.

3. The system of claim 1, wherein the plurality of separate conduits comprise a conduit for passage of volatile anesthetic, a conduit for sampling volatile anesthetic, a conduit for purging volatile anesthetic, and at least one conduit for pressure sensing.

4. The system of claim 3, wherein the conduits for passage of volatile anesthetic, sampling volatile anesthetic, and for purging volatile anesthetic, have larger internal diameters than the conduit(s) for pressure sensing.

5. The system of claim 1, wherein the external surface of the second portion of the connector comprises an outside diameter, wherein the outside diameter increases in a direction from the interface plug end toward the first portion.

6. The system of claim 1, further comprising an outer cover for the plurality of separate conduits.

7. The system of claim 2, wherein the plurality of separate conduits comprise a conduit for passage of volatile anesthetic, a conduit for sampling volatile anesthetic, a conduit for purging volatile anesthetic, and at least one conduit for pressure sensing.

8. The system of claim 7, wherein the conduits for passage of volatile anesthetic, sampling volatile anesthetic, and for purging volatile anesthetic, have larger internal diameters than the conduit(s) for pressure sensing.

9. The system of claim 2, wherein the external surface of the second portion of the connector comprises an outside diameter, wherein the outside diameter increases in a direction from the interface plug end toward the first portion.

10. The system of claim 4, wherein the external surface of the second portion of the connector comprises an outside diameter, wherein the outside diameter increases in a direction from the interface plug end toward the first portion.

11. The system of claim 1, wherein the connector comprises a rigid skeleton and a flexible shell, wherein the rigid skeleton is covered by and bonded to the flexible shell.

* * * * *